United States Patent [19]

Paudler

[11] 4,441,497

[45] Apr. 10, 1984

[54] UNIVERSAL SUTURE PASSER

[76] Inventor: Franklin T. Paudler, 13820 Somerset La. Southeast, Bellevue, Wash. 98006

[21] Appl. No.: 435,731

[22] Filed: Oct. 21, 1982

[51] Int. Cl.³ .................... A61B 17/06; A61B 17/04; A61B 17/34
[52] U.S. Cl. ............................ 128/339; 128/334 R; 128/329 R
[58] Field of Search .......... 128/334 R, 329 A, 329 R, 128/337, 339, 345, 303 R

[56] References Cited

U.S. PATENT DOCUMENTS

| 263,890 | 9/1882 | Gates | 128/339 |
| 621,337 | 4/1907 | Gibson | 128/326 |
| 2,295,848 | 9/1942 | Jones | 128/303 R |
| 2,715,486 | 8/1955 | Marcoff-Moghadam et al. | 128/339 |
| 2,883,096 | 4/1959 | Dawson | 128/339 |
| 3,517,128 | 6/1970 | Hines | 128/345 |
| 4,133,339 | 1/1979 | Naslund | 128/339 |

FOREIGN PATENT DOCUMENTS 1396 of 1910 United Kingdom ................ 128/339

OTHER PUBLICATIONS

American Jorn. of Opthalmology, Nov. 1971, vol. 72, No. 5, p. 1013, (FIG. 1).

Primary Examiner—C. Fred Rosenbaum
Assistant Examiner—C. W. Shedd
Attorney, Agent, or Firm—Seed and Berry

[57] ABSTRACT

A surgical tool for passing sutures during surgery comprises a plurality of elongated flexible members which are aligned longitudinally and joined at their corresponding ends. The members may be flexed outwardly to allow easy insertion of a suture therebetween. Sutures are pulled toward a joined end to secure them within the suture passer. The flexible members allow the tool to be used within confined areas and to pass suture along curved pathways. Multiple sutures may be inserted between the members at one time and pulled through the patient where necessary for sewing parts of the body together.

9 Claims, 4 Drawing Figures

U.S. Patent     Apr. 10, 1984     4,441,497
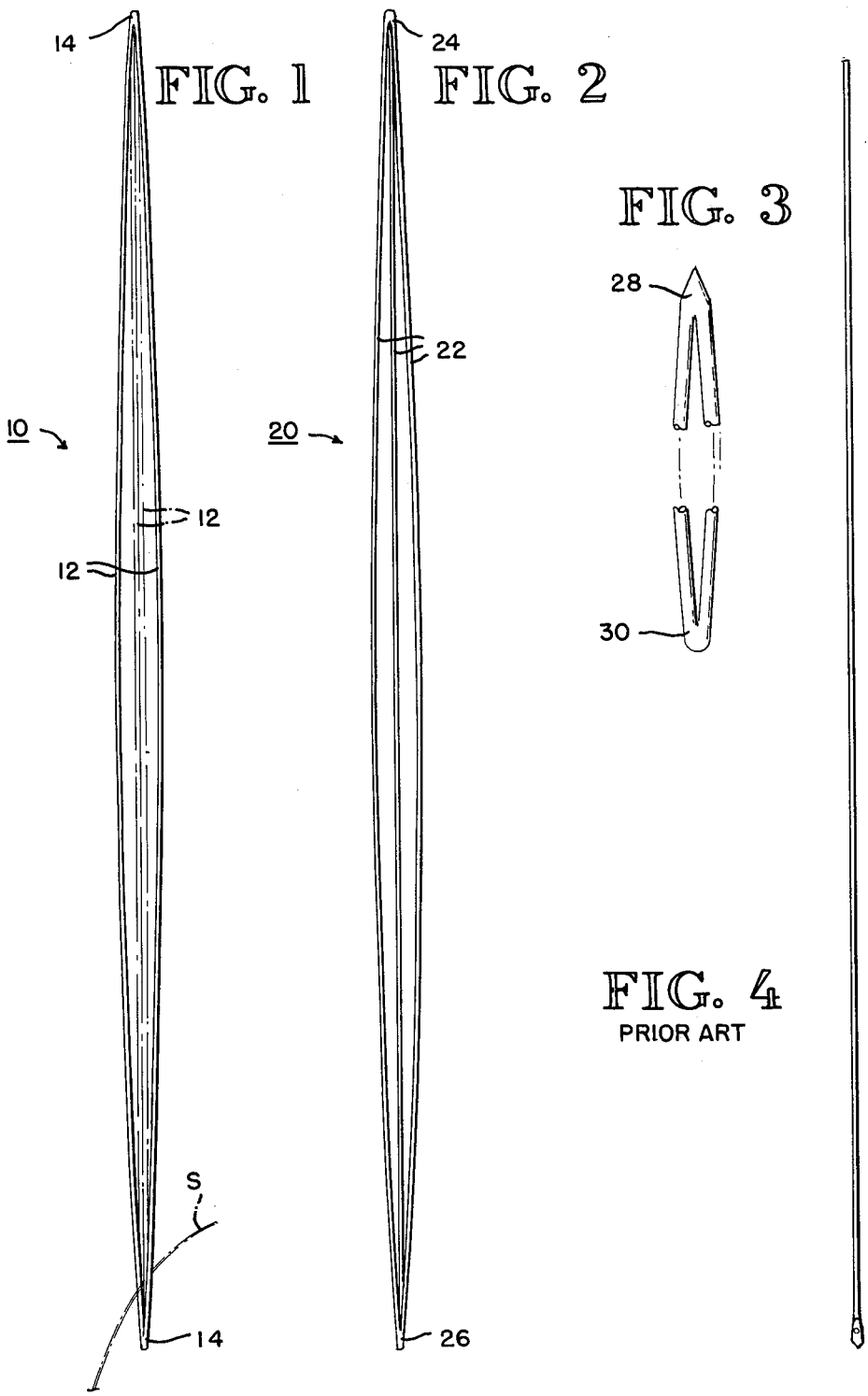

UNIVERSAL SUTURE PASSER

TECHNICAL FIELD

This invention relates to an improved surgical tool for passing sutures through bones, ligaments, and the like to sew them together, and more particularly, to such a tool which is suitable for passing sutures through knee and shoulder joints and regions of soft tissue.

BACKGROUND ART

Sutures are thread-like strands or fibers used during surgery to sew together parts of the human body. When sewing together parts of the body, a surgeon will generally insert the suture into a thin, elongated surgical tool known as a "suture passer" and pass the suture and suture passer through the body to form a series of stitches. If the portions of the body being sewn together undergo considerable stress, it may be necessary to use several strands of suture to adequately sew the body portions together.

Conventional suture passers are rigid stainless steel rods of approximately ⅛ inch in diameter and 9 inches in length. The leading edge of the rod is ground to a point, as illustrated in FIG. 4, and includes a small aperture through the ground portion for threading a suture therethrough. To drill an aperture in the suture passer of sufficient size for accepting a suture, the suture passer should be ⅛ inch or more in diameter.

Conventional suture passers such as described above and illustrated in FIG. 4 are designed to function as drill bits as well as a suture passers. Although a surgeon can readily pass a suture passer through soft tissue or fibrous tissue by merely applying forward pressure to the suture passer, it is necessary to drill a passageway through bone before passing a suture and suture passer therethrough. Conventional suture passers are designed to be attached to a drill and used as a drill bit to drill a passageway through bone. When the leading edge of the suture passer has passed through the bone and out the back side of the passageway, the surgeon will thread a suture through the aperture of the suture passer. The suture passer is then withdrawn through the passageway, pulling the suture from the back side to the front side of the passageway. Alternately, a separate drill bit may be used to create a passageway. The suture passer is then merely inserted through the passageway to receive a suture at the back side of the passageway and pull it to the front side of the passageway. It is also possible to first thread the suture passer and insert it through the passageway with the suture in place when the passageway has been pre-drilled.

It is preferred that suture passers be at least 7 to 9 inches long. Passageways through bones may be up to 3½ inches long. It is necessary to have adequate length to allow the leading edge of the suture passer to extend beyond the passageway to be threaded. The trailing end of the suture passer may have to pass through soft tissue on its way to the bone passageway and additionally must provide adequate room for the surgeon to handle the suture passer.

Although conventional suture passers work well for sewing together large bone segments in accessible areas, they are not well suited for sewing together ligaments or bones in confined areas, such as knee and shoulder joints. Because conventional suture passers are rigid instruments, they cannot be easily manipulated within the knee or shoulder joint to maneuver around anatomical parts or follow curved pathways. Sewing together ligaments or bones in these areas using arthroscopic surgery (in which only small incisions are made and the surgeon views the inside of the joint through a special view instrument known as an "arthroscope") has not been possible using conventional suture passers.

The unacceptability of conventional suture passers for use in areas which require flexibility has led to a number of makeshift surgical techniques for passing sutures through ligaments or bones in these areas. Many surgeons fasten loops at the end of a single wire and pass the wire through the ligament or bone needed to be connected. This technique is undesirable, however, as the bends which form in the wire at the loops are often sharp and capable of hanging up on soft tissue when passing through a knee joint. As minimizing damage to soft tissue is important for reducing patient recovery time, it is desirable to avoid damage to such tissue whenever possible.

Another drawback to this makeshift wire technique, as well as to conventional suture passers, is the inability to readily pass multiple sutures through part of the body at one time. Large ligaments often undergo sufficient stress to require multiple strands of sutures to repair them when they are torn. Consequently, it is advantageous to be able to pass multiple strands of suture through such ligaments with a single pass of a suture passer.

DISCLOSURE OF INVENTION

It is an object of this invention to provide a flexible suture passer for use in regions of the body such as knee and shoulder joints.

It is another object of the invention to provide a suture passer which may be easily threaded.

It is another object of this invention to provide such a suture passer which is capable of threading multiple strands of suture with a single pass.

It is another object of this invention to provide a suture passer which is suitable for use in arthroscopic surgery.

It is another object of this invention to provide a suture passer which will not catch soft tissue as it passes therethrough.

It is another of this invention to provide a suture passer which will have a small cross-sectional area to permit easy passage through tissue.

It is another object of this invention to provide a suture passer which is capable of puncturing fibrous tissue to pass sutures through ligaments or the like as well as passing through pre-drilled holes.

These and other objects of the invention, which will become more apparent as the invention is more fully described below, are obtained by providing a suture passer which comprises a plurality of thin, flexible wire members aligned in a generally parallel configuration and joined together at their ends. The wire members are spread apart for threading a suture or sutures therebetween. Two or more sutures may be held tightly between the wires by merely pulling the sutures tightly toward one end of the suture passer after threading them through the wires. A preferred embodiment of the suture passer includes both blunt and sharp ends for use alternately to puncture fibrous tissue or to pass through soft tissue or pre-drilled holes.

BRIEF DESCRIPTION OF THE DRAWINGS

FIG. 1 is an isometric view of a preferred embodiment of the invention including two wire members. The suture passer is illustrated in solid line a spread-apart position for threading a suture therethrough and in dotted line when in a contracted position.

FIG. 2 is an isometric view illustrating a preferred embodiment of the invention utilizing three wire members.

FIG. 3 is an isometric view of two ends of a preferred embodiment of the suture passer of this invention cut away at the center portion to illustrate in detail a rounded end and a sharpened end.

FIG. 4 is an isometric view of a conventional prior art suture passer.

BEST MODE FOR CARRYING OUT THE INVENTION

A suture passer 10 comprising a preferred embodiment of the present invention is illustrated in FIG. 1. Two wire members 12 of approximately the same length are aligned adjacent one another and joined at each end to form a flexible tool which includes an open space between the wire members. To secure a suture within the suture passer 10, a surgeon simply spreads the wire members 12 apart to enlarge the open space therebetween and passes the suture through the open space. Once in the open space, the suture is then pulled toward one of the joined ends 14 of the wire members 12 until the suture is held tightly between the wire members.

The suture passer 10 of FIG. 1 comprises two segments of stainless steel wire 12 which are aligned in a generally parallel position and joined at their corresponding ends 14 using standard microwelding techniques. Wire members 12 are approximately 0.030 inch in diameter and 9.5 inches in length. Ends 14 are rounded by the microwelding process and allow passage of the suture passer through soft tissue and around anatomical parts without causing damage.

A suture S may be inserted through the open space between the wire members 12 when the wire members are in the spread-apart position illustrated in FIG. 1. The suture S may then be pulled toward one of the ends 14 to the location shown in FIG. 1 to secure it between the wire members 12. After a first suture S has been secured in the suture passer 10, the securing process may be repeated with a second suture if it is desired to pass multiple sutures at one time.

A suture passer 20 comprising a second preferred embodiment of the invention is illustrated in FIG. 2. Three wire members 22 are aligned adjacent one another and joined at their corresponding ends 24, 26 by standard microwelding techniques. The resulting suture passer 20 functions in the same manner as the suture passer 10 having two wire members 12. The addition of a third wire member 22 creates an additional open space through which additional sutures S may be passed. When using a suture passer 20 having three wire members 20, a surgeon may secure up to five or six sutures within the suture passer. Thus, when stitching together a ligament which will undergo considerable stress, a surgeon may use a single pass of the suture passer 20 to stitch several sutures through the ligament.

The suture passer 20 illustrated in FIG. 2 includes one rounded end 26 and one sharpened end 24. The sharpened end 24 allows the suture passer 20 to be used as a suture needle for penetrating through ligaments or tendons. The sharpened ends 24 are fabricated by grinding the end 24 to a point after microwelding has taken place. If one end of the suture passer is sharpened, it is preferred that the other end be rounded to allow maximum versatility. A surgeon using such a suture passer may then elect to use the sharpened end for passing suture through tendons or ligaments or the rounded end if passing suture through soft tissue or predrilled passageways through bone. FIG. 3 illustrates in detail a two-wire member suture passer having a sharpened end 28 at one end and a rounded end 30 at the other. The sharpened ends are not designed to be used as drill bits, and, consequently, all passageways must be pre-drilled when using the suture passer 10, 20 of this invention.

In each of the embodiments disclosed herein, the wire members 12, 22 are comprised of stainless steel wire of approximately 0.030 inch in diameter. This size wire has been found acceptable both in terms of minimizing the total cross-section of the suture passer and maximizing manufacturing ease. It is desirable to provide a suture passer having a minimum cross-sectional area so that it may be easily passed through the body. Additionally, as stainless steel wire increases in diameter, it becomes less flexible and, consequently, harder to use in confined areas, such as the knee or shoulder joint. Flexibility is important in these areas where sutures may need to be passed through curved pathways. It has been found that wires of diameters substantially less than 0.030 inch are difficult to successfully microweld using conventional techniques. For these reasons, wires having a diameter of approximately 0.030 inch are preferred and stainless steel wires are used to fabricate the suture passers of this invention. Although the embodiments of the suture passers disclosed herein are fabricated with stainless steel wire members 12, 22, it is not intended that the invention be limited to suture passers having wire members of any particular material. The suture passers could be fabricated of metals other than stainless steel or even synthetic plastic material. It is important only that the material be capable of being sterilized before it is used, be sufficiently cohesive so that it will not break off inside a patient during use, and be sufficiently flexible so as to be preferably to conventional rigid suture passers.

In operation, it is preferred that the suture passers of this invention be used to pull sutures through the body rather than to push them through the body. Thus, when it is desirable to pass a suture through a given pathway, it is preferred that the suture passer be first inserted in a reverse direction along the pathway until the leading end of the suture passer projects outwardly a distance beyond the starting point of the pathway. The wire members 12, 22 of the suture passer are then separated and a suture or sutures secured within the suture passer as described above. Once the sutures are secured within the suture passer, the suture passer is withdrawn through the pathway to pull the suture forwardly along the pathway. Pulling the suture in this manner ensures that the suture will remain securely held within the suture passer as the forces acting on the suture will tend to push it rearwardly into the end of the suture passer in which it is secured. The embodiments of the suture passer illustrated herein are approximately 9½ inches in length. Although the length of the suture passer is not critical to this invention, it has been found that suture passers of this length are well suited for use in surgery, as they provide sufficient length to extend through the body and project outwardly to allow insertion of sutures at the leading end while leaving adequate room for the trailing end of the suture passer to function as a handle for the surgeon. Suture passers of substantially greater length than those illustrated in the embodiments disclosed herein tend to be awkwardly long for many uses, although extra length may be necessary for particular operations.

Although the suture passer of this invention has been disclosed herein with respect to particular embodiments thereof, it is not intended that the invention be limited to these particular embodiments, but rather that the invention include all embodiments which are within the spirit of the invention.

I claim:

1. An apparatus for guiding sutures through body tissue or the like comprises:
   a plurality of elongated flexible members of approximately equal length, the members disposed alongside one another and joined together at each end to define an open space between each pair of members for receiving a suture therethrough, each open space decreasing in size as it approaches one of the joined ends of the members to define a region adjacent such joined end for securing a suture between the members.

2. The apparatus of claim 1 wherein one of the joined ends includes a rounded exterior surface for maneuvering through soft tissue or around anatomical parts.

3. The apparatus of claim 1 or claim 2 wherein the exterior surface of at least one of the joined ends is ground to a point to allow the apparatus to function as a needle for penetrating fibrous tissue such as ligaments.

4. An apparatus for passing sutures during surgery which comprises:
   a plurality of elongated flexible wires of substantially equal length longitudinally with respect to one another and joined at their corresponding ends, the wires being closely spaced apart adjacent at least one joined end for securing sutures therebetween, the wires flexing outward to allow easy insertion of a suture therebetween.

5. The apparatus of claim 4 wherein one of the joined ends includes a rounded exterior surface for maneuvering through soft tissue or around anatomical parts.

6. The apparatus of claim 4 or claim 5 wherein the exterior surface of at least one of the joined ends is ground to a point to allow the apparatus to function as a needle for penetrating fibrous tissue such as ligaments.

7. An apparatus for guiding sutures through body tissue or the like which comprises:
   a pair of elongated members of approximately equal length, the members being aligned alongside one another and joined rigidly at their corresponding ends, the members being flexible to permit separation of the members at locations spaced apart from the joined ends for easy insertion of a suture between the members, at least one of the joined ends defining a region between the members adjacent such joined end for wedging a suture between the members to hold it securely within the apparatus during use.

8. The apparatus of claim 7, additionally including a third elongated member joined at its ends to the corresponding ends of the pair of elongated members, the third member defining an additional region for wedging sutures, the third member facilitating the passage of multiple sutures through body tissue at one time.

9. A method of passing a plurality of sutures through a pathway at one time, the pathway having a starting point and a terminus, which comprises the steps of:
   (a) inserting a suture passer through the pathway from the terminus to the starting point until the leading end of the suture passer projects outwardly from the pathway a distance beyond the starting point, the suture passer comprising:
      (i) a pair of elongated members of approximately equal length, the members being aligned alongside one another and joined rigidly at their corresponding ends, the members being flexible to permit separation of the members at locations spaced apart from the joined ends for easy insertion of a suture between the members, at least one of the joned ends defining a region between the members adjacent such joined end for wedging a suture between the members to hold it securely within the apparatus during use;
   (b) spreading apart the wire members of the suture passer to enlarge the open spaces therebetween;
   (c) inserting a plurality of sutures through the open spaces between the wire members;
   (d) pulling the sutures toward the leading end of the suture passer to secure the sutures within the suture passer;
   and
   (e) withdrawing the suture passer from the pathway to pull the sutures from the starting point to the terminus of the pathway.

* * * * *

UNITED STATES PATENT AND TRADEMARK OFFICE
CERTIFICATE OF CORRECTION

PATENT NO. : 4,441,497
DATED : April 10, 1984
INVENTOR(S) : Franklin T. Paudler

It is certified that error appears in the above—identified patent and that said Letters Patent is hereby corrected as shown below:

Column 6, line 35, delete "joned" and substitute therefor --joined--.

Signed and Sealed this

Fourth Day of September 1984

[SEAL]

Attest:

GERALD J. MOSSINGHOFF

Attesting Officer

Commissioner of Patents and Trademarks